United States Patent
Holl et al.

(10) Patent No.: US 10,592,691 B2
(45) Date of Patent: Mar. 17, 2020

(54) METHOD AND SYSTEM FOR GRANTING A USER ACCESS TO A MEDICAL SYSTEM

(71) Applicant: General Electric Company, Schenectady, NY (US)

(72) Inventors: Thomas Holl, Zipf (AT); Roland Rott, Munich (DE)

(73) Assignee: General Electric Company, Schenectady, NY (US)

( * ) Notice: Subject to any disclaimer, the term of this patent is extended or adjusted under 35 U.S.C. 154(b) by 159 days.

(21) Appl. No.: 15/639,875

(22) Filed: Jun. 30, 2017

(65) Prior Publication Data
US 2019/0005263 A1    Jan. 3, 2019

(51) Int. Cl.
| | |
|---|---|
| *H04L 29/08* | (2006.01) |
| *G06F 21/62* | (2013.01) |
| *G16H 40/63* | (2018.01) |
| *G16H 40/67* | (2018.01) |
| *G06F 19/00* | (2018.01) |

(52) U.S. Cl.
CPC ......... *G06F 21/6245* (2013.01); *G16H 40/63* (2018.01); *G16H 40/67* (2018.01); *H04L 67/141* (2013.01); *H04L 67/18* (2013.01); *G06F 19/321* (2013.01); *G06F 19/328* (2013.01); *H04L 67/143* (2013.01)

(58) Field of Classification Search
CPC .. G06F 21/6245; G06F 19/328; G06F 19/321; H04L 67/141; H04L 67/18; H04L 67/143
See application file for complete search history.

(56) References Cited

U.S. PATENT DOCUMENTS

| | | | | |
|---|---|---|---|---|
| 9,218,452 | B2* | 12/2015 | Varna | G16H 10/60 |
| 2005/0027995 | A1* | 2/2005 | Menschik | G06F 19/321 |
| | | | | 713/193 |
| 2007/0061393 | A1* | 3/2007 | Moore | G06F 19/325 |
| | | | | 709/201 |
| 2008/0172737 | A1* | 7/2008 | Shen | G16H 10/60 |
| | | | | 726/21 |
| 2010/0115609 | A1* | 5/2010 | Spence | G06F 19/3418 |
| | | | | 726/19 |
| 2015/0223891 | A1* | 8/2015 | Miller | A61B 5/1171 |
| | | | | 726/19 |

\* cited by examiner

*Primary Examiner* — Khoi V Le
(74) *Attorney, Agent, or Firm* — Dean D. Small; The Small Patent Law Group, LLC

(57) ABSTRACT

Method includes determining that a personal communication device is within a designated range of a medical system. The personal communication device is configured to transmit and receive data through a telecommunication network. The method also includes receiving an identifying signal from the personal communication device while within the designated range of the medical system for identifying a user associated with the personal communication device. The method also includes determining that the user associated with the personal communication device is permitted to use the medical system. The method also includes opening a session for the user to use the medical system. The method also includes establishing a dedicated link between the personal communication device and the medical system such that other users are unable to use the medical system during the session. The method also includes closing the session, thereby permitting the other users to use the medical system.

20 Claims, 6 Drawing Sheets

METHOD AND SYSTEM FOR GRANTING A USER ACCESS TO A MEDICAL SYSTEM

BACKGROUND

The subject matter disclosed herein relates generally to systems and methods for changing operator preferences of a medical system.

A medical system is typically operated by users (or operators) that have been trained for the medical system and, in some cases, specifically trained in a certain application of that imaging system. Such systems include medical imaging systems, such as an ultrasound system, magnetic resonance imaging (MRI) system, computed tomography (CT) system, positron emission tomography (PET) system, and single photon emission computed tomography (SPECT) system. An ultrasound system typically includes an ultrasound probe that is applied to a patient's body and a workstation that is operably coupled to the probe. The probe transmits and receives ultrasound signals that are processed into an ultrasound image. The workstation may show the operator the ultrasound image and may enable the operator to control operation of the probe. To this end, the workstation may have a user interface that includes user-selectable elements (e.g., tangible or virtual knobs, levers, tabs, buttons, and the like) for controlling operation of the ultrasound system.

In some clinical environments (e.g., hospital, doctor's office, and the like), a single ultrasound system may be used to examine several people in a day and/or may be used in different types of examinations. By way of example only, a single ultrasound imaging system may be used to image a baby in a woman's uterus, to image various organs in a patient's abdomen, to image the heart, or to image different parts of the vascular system. Moreover, a single ultrasound system may be used by a number of different operators. Each of the operators may prefer different settings for operating the ultrasound system.

Because medical systems may be accessed by different users, it is desirable that the medical systems protect patient privacy and do not compromise security of the enterprise. For example, systems that allow access to patient data should be consistent with regulatory requirements, such as those relating to the Health Insurance Portability and Accountability Act (HIPAA). Thus, it is desirable to limit access to the medical systems to those users that are authorized. Conventional systems require each user to take time and interact with the system. For example, it may be necessary for the user to login using a username and password. After confirming the username and password are correct, the system may then allow the user access to the system. In some cases, it may take time for the system to load the desired programs.

In addition to the above, an operator of an ultrasound system may have to change one or more settings of the ultrasound system or to select a different workflow for the ultrasound system. Even when an ultrasound system is exclusively used for a particular examination (e.g., echocardiograms) different operators of the ultrasound system may have different preferred settings. Such preferences may affect the quality of images and/or may affect usability of the ultrasound system. However, changing the settings of an ultrasound system may be time consuming and, in some cases, a user may not be able to remember the different settings that he or she prefers until the user has already begun an examination.

BRIEF DESCRIPTION

In an embodiment, a method is provided that includes determining that a personal communication device is within a designated range of a medical system. The personal communication device is configured to transmit and receive data through a telecommunication network. The method also includes receiving an identifying signal from the personal communication device while within the designated range of the medical system for identifying a user associated with the personal communication device. The method also includes determining that the user associated with the personal communication device is permitted to use the medical system. The method also includes opening a session for the user to use the medical system. The method also includes establishing a dedicated link between the personal communication device and the medical system such that other users are unable to use the medical system during the session. The method also includes closing the session, thereby permitting the other users to use the medical system.

In some aspects, the method also includes receiving predetermined operational settings from the personal communication device while within the designated range of the medical system. The predetermined operational settings affect operation of the medical system. The medical system may be at least one of an imaging system, diagnostic system, therapeutic system, monitoring system, or surgical system. The method may also include communicating changes to the predetermined operational settings from the medical system to the personal communication device during the session of the user with the medical system.

In some aspects, the medical system includes a predetermined space where the personal communication device is positioned to provide the identifying signal. The predetermined space includes or is positioned adjacent to a near-field communication (NFC) device.

In some aspects, the determining that the user associated with the personal communication device is permitted to use the medical system includes receiving an unlocked signal from the personal communication device. The unlocked signal is based on user inputs provided by the user while within the designated range of the medical system.

In some aspects, the personal communication device is configured to present a predetermined unlock screen to the user prior to granting access to the personal communication device. The predetermined unlock screen is configured to receive correct user inputs to allow access to the personal communication device. The determining that the user associated with the personal communication device is permitted to use the medical system includes receiving an unlocked signal from the personal communication device in response to the user entering the correct user inputs.

In some aspects, the determining that the personal communication device is operably near the medical system is determined using a first wireless technology. The method also includes transferring data between the medical system and the personal communication device using a second wireless technology.

In some aspects, the ending the session includes determining that the personal communication device is not operably near the medical system.

In some aspects, the medical system includes a handheld device to be controlled by the user. The method also includes locking the handheld device to a base of the medical system before the session and unlocking the handheld device from the base during the session.

In some aspects, the medical system is a first medical system, the method also includes determining that the personal communication device is operably near a second medical system; receiving an identifying signal from the personal communication device while within the designated range of the second medical system; determining that the user associated with the personal communication device is permitted to use the second medical system and opening a session for the user to use the second medical system; establishing a dedicated link between the personal communication device and the second medical system such that other users are unable to access the second medical system during the session; and ending the session, thereby permitting the other users to use the second medical system.

In an embodiment, a system is provided that includes one or more processors configured to execute programmed instructions stored in memory. Optionally, the system may include a user interface configured to receive user inputs from a user. The one or more processors, when executing the programmed instructions, are configured to: determine that a personal communication device is within a designated range of a medical system; receive an identifying signal from the personal communication device while within the designated range of the medical system for identifying the user associated with the personal communication device; determine that the user associated with the personal communication device is permitted to use the medical system and open a session for the user to use the medical system; establish a dedicated link between the personal communication device and the medical system such that other users are unable to access the medical system during the session; and end the session, thereby permitting the other users to use the medical system.

In some aspects, the one or more processors, when executing the programmed instructions, also perform the following operations: receive predetermined operational settings from the personal communication device while within the designated range of the medical system, the predetermined operational settings affecting operation of the medical system; and communicate changes to the predetermined operational settings from the medical system to the personal communication device during a session of the user with the medical system.

In some aspects, the medical system includes a handheld device to be controlled by the user. The one or more processors are configured to lock the handheld device to a base of the medical system before the session and unlock the handheld device from the base during the session.

In some aspects, the determining, by the one or more processors, that the user associated with the personal communication device is permitted to use the medical system includes receiving an unlocked signal from the personal communication device that is different than and transmitted separately from the identifying signal.

In some aspects, the determining, by the one or more processors, that the personal communication device is operably near the medical system is determined using a first wireless technology. The one or more processors are also configured to transfer data between the medical system and the personal communication device using a second wireless technology.

In some aspects, the ending the session includes determining that the personal communication device is not operably near the medical system.

In an embodiment, a method is provide that includes transmitting, within a designated range of a medical system, an identifying signal for identifying a personal communication device. The method also includes receiving, at the personal communication device, a request to confirm that a user of the personal communication device desires access to the medical system. The method also includes transmitting a signal that confirms the user of the personal communication device desires access to the medical system. The method also includes transmitting predetermined operational settings for the medical system from the personal communication device to the medical system. The predetermined operational settings are stored on the personal communication device. The method also includes receiving changes to the predetermined operational settings to the personal communication device during a session of the user with the medical system. The method also includes storing the changes to the predetermined operational settings.

In some aspects, the method also includes transmitting data that indicates the personal communication device has been unlocked while within the designated range.

In some aspects, the transmitting the identifying signal for identifying the personal communication device is transmitted in accordance with a first wireless technology and the transmitting predetermined operational settings is transmitted in accordance with a different second wireless technology.

In one or more embodiments, the medical system is an ultrasound system that includes an ultrasound probe. In one or more embodiments, the personal communication device includes at least one of a mobile phone, a portable computer, or a wearable device. The personal communication device may be at most three kilograms.

DETAILED DESCRIPTION

Figure 1:
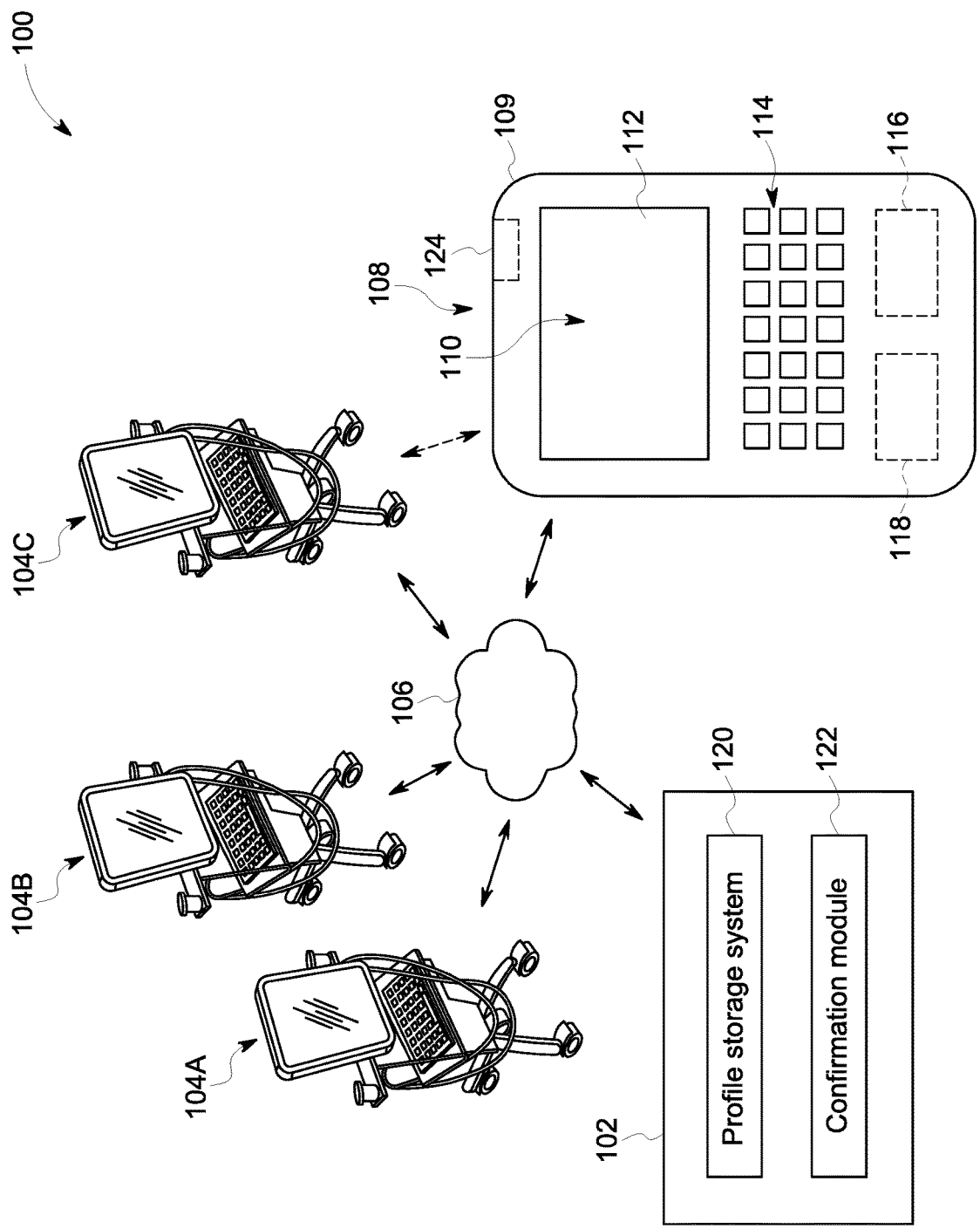
FIG. 1 illustrates a system network in accordance with one embodiment that includes a plurality of medical systems.

Embodiments described herein include or are configured to operate with personal communication devices that may be used to grant a user access to a medical system. Other embodiments include systems (e.g., a medical system or a system network having a plurality of medical systems), methods, and computer readable media that are configured to interact with such personal communication devices. The personal communication devices typically include an antenna that is capable of communicating (e.g., transmitting and/or receiving signals) that may be used to identify and/or authorize the user of the personal communication device. Signals for communicating may be generated directly by the personal communication device (e.g., power of the personal communication device is used to make the signals through the antenna). In some cases, the signals for communicating are passively generated (e.g., energy is provided by a reader that causes a tag to respond with the signals).

The personal communication devices are not necessarily used exclusively for identification and/or authorization purposes. The personal communication devices may have functions other than identifying a user of the personal communication device. For example, the personal communication devices may be used to view images, read data, analyze data, and the like. As used herein, a "personal communication device" means the device is at most three (3.0) kilograms (kg). In particular embodiments, the personal communication device is at most 2.0 kg, at most 1.0 kg, at most 0.5 kg, or, more particularly, at most 0.25 kg. Non-limiting examples of the personal communication devices include a mobile phone, a portable computer (e.g., laptop, notebook, or tablet), or a wearable smart device (e.g., headset, smart glasses, smartwatch, activity tracker). A wearable smart device is a device that performs additional functions other than identifying and/or authorizing the wearer. Each of these examples is capable of transmitting and receiving data through a wireless communication technology.

Embodiments may be configured to use one or more wireless communication technologies. As such, the systems include the necessary hardware and software for utilizing the wireless communication technology or technologies. A wireless communication technology may be a short-range wireless communication technology, a medium-range wireless communication technology (e.g., WiMax), or a wide-area wireless communication technology (e.g., cellular). The short-range wireless communication technology is configured for communicating within a range that is at most 100 meters. In some embodiments, the short-range wireless communication technology is configured for communicating within a range that is at most 50 meters. In certain embodiments, the short-range wireless communication technology is configured for communicating within a range that is at most 30 meters or at most 10 meters. In particular embodiments, the short-range wireless communication technology is configured for communicating within a range that is at most 1 meter or at most 25 centimeters. In more particular embodiments, the short-range wireless communication technology is configured for communicating within a range that is at most 10 centimeters. Examples of short-range wireless communication technologies are Bluetooth, infrared, near field communication (NFC), ultra-wideband (UWB), Wireless USB, Zigbee, Wi-Fi, and radiofrequency identification (RFID). Embodiments may be capable of communicating using one or a plurality of wireless communication technologies.

In some embodiments, the personal communication device is configured to communicate through an established telecommunication network in addition to communicating with a short-range wireless technology. More specifically, the personal communication device may communicate through a proprietary network infrastructure operated by a telecom carrier (e.g., Verizon, AT&T, Sprint). The personal communication device may communicate through a prearranged plan with a telecom carrier.

In some embodiments, the personal communication device is configured to store a user profile or a number of different user profiles in which each user profile includes information relating to a user (or operator) of a medical system. The user profile may be associated with a user (e.g., owner or possessor) of the personal communication device. For example, a smartphone may store one or more user profiles of the user of the smartphone. As such, a healthcare provider may use his or her smartphone to store the user profile and communicate the user profile to a system (e.g., medical system). Other personal communication devices may be used, such as portable computers or wearable devices.

As used herein, a "user profile" (which may also be referred to as "operator profile") includes a collection of information or data relating to a user of a medical system. The user profile may constitute a package of information or data that may be communicated to different components of a system network. A user profile may identify predetermined operational settings of a medical system that are designated or selected from a number of potential operational settings. The predetermined operational settings may be settings selected by the operator for being automatically loaded into the medical system. In particular embodiments, the predetermined operational settings may be automatically loaded into a program of the medical system.

A single person (e.g., doctor, nurse, technician, or other suitable person) may have multiple user profiles. For instance, a person may have different user profiles for different medical imaging modalities (e.g., a user profile for ultrasound and a different user profile for PET/CT); a person may have different user profiles for different models of a common imaging modality (e.g., a first ultrasound system and a second ultrasound system); or a person may have different user profiles for a common medical system (e.g., a user profile for echocardiography and a different user profile for obstetric ultrasound imaging). For example, a single user may have multiple profiles for the different applications that could be performed by a single medical system. As another example, a single user may have multiple profiles for the different workflows that a single application can perform.

In some embodiments, the user profile includes additional information. For example, the user profile may also include one or more of medical image(s); statistical information relating to the operator (e.g., number of scans performed, different medical systems used); accreditation data; and documents that the operator wishes to have readily available. In some cases, the user profile may be directly accessed by the operator (e.g., through the medical system or through a personal communication device) and changes may be made directly to the user profile. For example, a web-based application on the medical system, a personal computer, or a personal communication device may show the operator the data/information that is stored with the user profile, including the predetermined operational settings of the various medical systems for the operator. The application may permit the operator to make changes to the user profile, such as changes to the predetermined operational settings. Accordingly, the operator may change the user profile at a location other than the medical system.

The following detailed description of various embodiments will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., modules, processors, or memories) may be implemented in a single piece of hardware (e.g., a general purpose signal processor or a block of random access memory, hard disk, or the like) or multiple pieces of hardware. Similarly, the programs may be standalone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 illustrates a system network 100 that includes a server system 102 and a plurality of medical systems 104A-104C that are configured to communicate with one another and/or the server system 102. The system network 100 may also include one or more personal communication devices 108. The medical systems 104A-104C, the devices 108, and the server system 102 may communicate through a network 106, which may include, for example, one or more of the Internet, a wide area network (WAN), a local area network (LAN), campus area network, and the like. The medical systems 104A-104C may be various types of medical systems, such as an ultrasound system, a magnetic resonance imaging (MM) system, a computed tomography (CT) system, a positron emission tomography (PET) system, and/or a single photon emission computed tomography (SPECT) system, among others.

As shown in FIG. 1, in certain embodiments, the medical systems 104A-104C are ultrasound systems and, more particularly, are mobile ultrasound systems that are capable of being moved from one location to another location (e.g., from one room or floor to another room or floor). However, the medical systems 104 may have various sizes and configurations. As described herein, the medical systems 104 are not required to be the same modality. A single person may be associated with multiple user profiles for the different medical imaging modalities, medical imaging systems, and workflows. Each personal communication device 108 may be associated with a user (e.g., person) and may be used to store one or more user profiles.

The server system 102 includes a computing system that provides services to other components of the system network 100 (e.g., the medical systems 104 and/or the personal communication devices 108) and may communicate through the network 106. The server system 102 may include one or more servers that are configured to manage resources of the system network 100. For example, the server system 102 may receive data, process the data in a designated manner, store the data, and/or transmit the data to other components that are communicatively coupled to the telecommunications network 106. The server system 102 may respond to requests from the other components. The server system 102 may have a distinct location with respect to the other components. For example, the server system 102 may be remote from the medical systems 104A-104C and from the personal communication devices 108. In FIG. 1, the server system 102 appears to have one location, however; it should be understood that the server system 102 may comprise several components that have separate locations.

In certain embodiments, personal communication devices 108 are configured to store the user profile(s). Alternatively or in addition to the devices 108, the server system 102 includes a profile-storage system 120 that is configured to store user profiles of operators that use the medical systems 104 of the system network 100. As described above, the user profiles may include information or data that identifies predetermined operational settings for a user of a medical system. Each operational setting may be designated or selected from a number of potential operational settings. The predetermined operational settings may be selected by the operator that is associated with (e.g., that corresponds to) the user profile. In some cases, the operational settings are selected by the user as preferred operational settings such that the selected operational settings are loaded into the medical system each time the medical system is initiated or loaded into an application each time the application is initiated. In some embodiments, the operational settings may be the operational settings that were last used by the operator prior to logging off of the medical system or the application.

The medical systems 104 and the personal communication devices 108 are configured to communicate with one another. In particular embodiments, the personal communication device 108 may communicate directly with the desired medical system 104. For example, the personal communication device 108 and the desired medical system 104 may communicate directly through a short-range wireless technology. Alternatively or in addition to the above, the personal communication device 108 may be configured to communicate with the desired medical system 104 through the network 106. In some embodiments, the personal communication device 108 and the desired medical system 104 may communicate directly through a first wireless technology (e.g., NFC). For example, the personal communication device 108 and the desired medical system 104 may communicate to grant the user of the personal communication device 108 access to the medical system 104. After granting access, the personal communication device 108 and the desired medical system 104 may then communicate through a second wireless technology (e.g., WiFi, cellular, etc.) using, for example, the network 106. In such instances, larger amounts of data may be transmitted using the second wireless technology.

In particular embodiments, the personal communication device 108 may determine the user profile that should be used with the medical system 104 that the personal communication device 108 is directly communicating with. For example, the personal communication device 108 may identify at least one of the modality of the medical system 104, a model of the medical system 104, or a program of the medical system 104 and use the identity (or identities) to select the user profile that will be communicated to the medical system 104.

The personal communication device 108 may identify the user profile(s) that is stored within the personal communication device 108 and send the user profile to the medical system 104. Alternatively or in addition to the above, the profile-storage system 120 may be configured to communicate (e.g., transmit) one or more user profiles to the medical system 104. For example, after determining that the user of the personal communication device 108 may have access to the medical system, a user profile may be retrieved from the profile-storage system 120.

In other embodiments, the server system 102 and/or the medical system 104 may include a confirmation module 122 that is configured to receive identifying data from the personal communication device and confirm that the identifying data corresponds to a user profile. The identifying data may be, for example, a username and password that are used by the operator or other information. The identifying data may also be a unique code or token associated with the user of the personal communication device 104.

In some embodiments, the user profile is requested by the medical system when the operator is initially communicating with the medical system. For example, after granting access to the medical system, the medical system may request the user profile from the profile-storage system. In other embodiments, the user profile is requested only after the operator has initiated a certain program on the medical system 104A. After the identity of the operator is confirmed, the profile-storage system 120 may select the user profile that is associated with the operator from the other user profiles and transmit the user profile to the medical system 104.

In one or more embodiments, changes to the predetermined operational settings may be made by the user during operation of the medical system 104. The predetermined operational settings may be saved and stored with the personal communication device 108 and/or the profile-storage system.

The personal communication devices 108 may constitute portable handheld devices, such as smartphones, tablet computers, and the like. Portable handheld devices may be dimensioned to be easily carried by an average adult. For example, the personal communication device 108 may have a housing 109 that is dimensioned to be carried by the operator. As shown, the personal communication device 108 may include a user interface 110 that includes a personal display 112 and a plurality of user-selectable elements 114. The user interface 110 may include hardware, firmware, software, or a combination thereof that enables an operator (e.g., an owner of the personal communication device 108) to directly or indirectly control operation of the personal communication device 108.

The user-selectable elements 114 may be activated by the operator to provide user inputs to the personal communication device 108. The user-selectable elements 114 may include keys of a keyboard, switches, a touchpad, and the like. The user-selectable elements 114 may be physical or virtual. For instance, the personal display 112 may be a touch-sensitive display (e.g., touchscreen) that can detect a presence of a touch from the operator (e.g., owner of the personal communication device 108) and can also identify a location of the touch in the display area. The touch may be applied by, for example, at least one of an operator's hand, stylus, or the like. As such, the touch-sensitive display may receive user inputs from the operator and also display information to the operator.

The personal communication device 108 also includes a device controller 116 (e.g., having one or more modules), one or more device storage components 118 (e.g., memory), and one or more communication ports 124. The device controller 116 controls operation of the personal communication device 108 and may include a plurality of modules for carrying out other functions of the personal communication device 108. The device storage component 118 may include storage components that are integral to the personal communication device 108 and may also include removable storage components 118 (e.g., SIM cards). As will be described in greater detail below, the device storage component 118 may function as a profile-storage system and store one or more user profiles associated with the operator (e.g., owner of the personal communication device 108). The communication port 124 may include hardware and/or software components that are configured to communicate data between the personal communication device 108 and the other components of the system network 100, such as the server system 102. For example, the communication ports 124 may be an antenna or a universal serial bus (USB) port. In some examples, the communication ports 124 may be characterized as input/output ports. In such cases where the personal communication device 108 is a smartphone or tablet computer, the communication port 124 may be an antenna that is used for communication in the telecommunications network 106 and in other telecommunications networks.

During operation of the personal communication device 108, the personal display 112 may include or form the user-selectable elements 114. For instance, graphical objects shown on the personal display 112 may resemble buttons, switches, sliders, and the like. In some embodiments, a locked screen may initially appear to the user of the personal communication device 108. The locked screen may include a plurality of user-selectable elements 114 (e.g., alphanumeric characters). The user may enter correct user inputs to access the personal communication device 108. For example, the user may enter a passcode (e.g., series of alphanumeric characters) to access the personal communication device 108 such that the personal communication device 108 is fully functional to the user. Alternatively, the user may touch the personal display 112 in a designated manner (e.g., touch and slide the user's fingers in one or more directions) to access the device. In particular embodiments, the personal communication device 108 may communicate with a system (e.g., the medical system or system network) in response to entering the correct user inputs.

The system network 100 may be characterized as a cloud-computing network. For example, many of the resources of the system network 100 may be shared by various components of the system network 100. The server system 102 may be configured to perform similar services for each of the medical systems 104 and/or the personal communication devices 108. More specifically, the server system 102 may be configured to operate or execute identical or similar algorithms for each of the medical systems 104 and/or the personal communication devices 108. The services may relate to analysis and/or processing of medical images.

Figure 2:
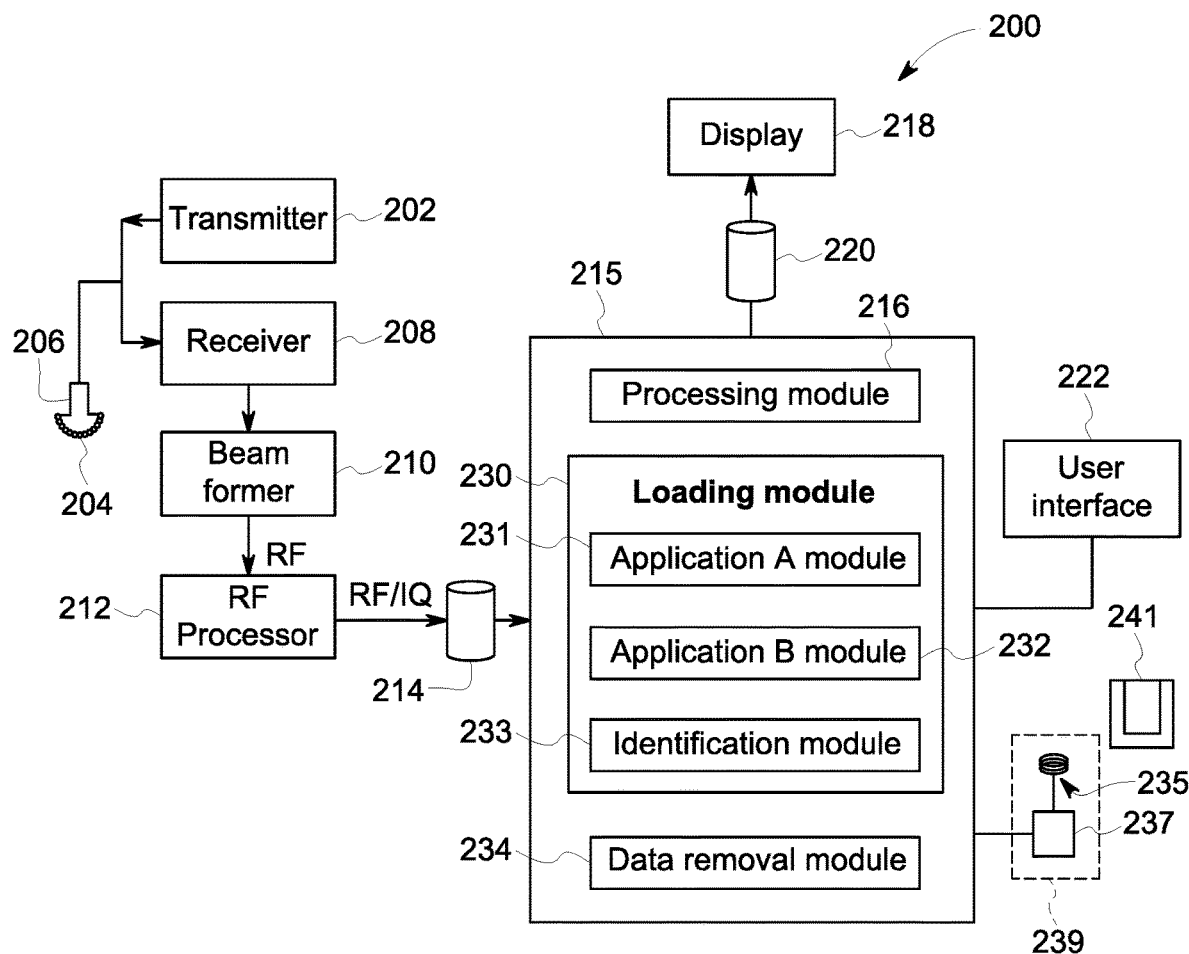
FIG. 2 illustrates a block diagram of a medical system in accordance with one embodiment.

FIG. 2 illustrates a block diagram of an ultrasound system 200 according to one embodiment. The ultrasound system 200 may be one of the medical systems 104A-104C (FIG. 1) and be part of the system network 100 (FIG. 1). In the illustrated embodiment, the ultrasound system 200 includes a transmitter 202 that drives an array of elements 204, for example, piezoelectric crystals, within a transducer (or probe) 206 to emit pulsed ultrasonic signals into a body or volume (not shown). A variety of geometries may be used and the transducer 206 may be provided as part of, for example, different types of ultrasound probes. The ultrasonic signals are back-scattered from structures in the body, for example, blood cells or muscular tissue, to produce echoes that return to the elements 204. The echoes are received by a receiver 208. The received echoes are provided to a beamformer 210 that performs beamforming and outputs an RF signal. The RF signal is then provided to an RF processor 212 that processes the RF signal. Alternatively, the RF processor 212 may include a complex demodulator (not shown) that demodulates the RF signal to form IQ data pairs representative of the echo signals. The RF or IQ signal data may then be provided directly to a computer-readable memory 214 for storage (for example, temporary storage).

The ultrasound system 200 also includes a system controller 215 that includes a plurality of modules. The system controller 215 is configured to control operation of the ultrasound system. For example, the system controller 215 may include a processing module 216 that processes the acquired ultrasound data (for example, RF signal data or IQ data pairs). The processing module 216 may prepare frames of ultrasound information (e.g., ultrasound images) for display on a display device 218. The processing module 216 is adapted to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography.

Acquired ultrasound information may be processed in real-time during an imaging session (or scanning session) as the echo signals are received. Additionally or alternatively, the ultrasound information may be stored temporarily in the memory 214 during an imaging session and processed in less than real-time in a live or off-line operation. A computer-readable image memory 220 is included for storing processed frames of acquired ultrasound information that are not scheduled to be displayed immediately. The image memory 220 may comprise any known data storage medium, for example, a permanent storage medium, removable storage medium, and the like.

The system controller 215 is connected to a user interface 222 that may enable control of at least some operations of the processing module 216 and is configured to receive user inputs from a user of the system network 100. In some embodiments, the user interface 222 includes the display device 218 and is configured to present information relating to the patient, including diagnostic ultrasound images to the user for review, diagnosis, and analysis. The user interface 222 (or the display device 218) may automatically display, for example, planes from two-dimensional (2D) and/or three-dimensional (3D) ultrasound data sets stored in the memory 214 or the image memory 220. One or both of the memory 214 and the memory 220 may store 3D data sets of the ultrasound data, where such 3D data sets are accessed to present 2D and 3D images. The processing of the data, including the data sets, is based in part on user inputs, for example, user selections received at the user interface 222.

In operation, the ultrasound system 200 acquires data, for example, volumetric data sets by various techniques (for example, 3D scanning, real-time 3D imaging, volume scanning, 2D scanning with transducers having positioning sensors, freehand scanning using a voxel correlation technique, scanning using 2D or matrix array transducers, and the like). Ultrasound images are displayed to an operator or user of the ultrasound system 200 on the display device 218.

The system controller 215 also includes a loading module 230, which may include a plurality of sub-modules 231-233. The loading module 230 is configured to load an application for operating the medical system, which may include, for example, loading operational settings from a portable user profile. The loading may include loading the operational settings when an application is initiated and may also include updating or modifying an active application with the operational settings of the user profile. The loading module 230 may be configured to load application modules, such as Application A module 231 and Application B module 232. The application modules 231, 232 may correspond to stored programs or applications that are configured to guide the user along predetermined workflows. For example, Application A module 231 may correspond to a liver/gallbladder imaging program that guides the user in obtaining ultrasound images of the liver and/or gallbladder. The Application B module 232 may correspond to an echocardiogram imaging program that includes a workflow that guides the user in obtaining ultrasound images of the heart. When application modules are initiated, the loading module 230 may be configured to load the corresponding program with predetermined operational settings of a user profile.

Alternatively, the loading module 230 may load the predetermined operational settings of the user profile after the programs are already active. For instance, when an application is open, the user may select a user profile from a list of user profiles.

The system controller 215 is communicatively coupled to an antenna 235 of the system 200. As shown, the antenna 235 is communicatively coupled to the system controller 215 through a wireless controller 237. The antenna 235 and the wireless controller 237 may be configured to communicate in accordance with a predetermined wireless communication technology, suggest as a short-range wireless communication technology (e.g., NFC). In some embodiments, the system 200 includes a reader device 239 that includes the antenna 235 and the wireless controller 237.

Personal communication devices may be configured to be positioned adjacent to the reader device 239 to communicate with the system 200. For example, the system 200 may include a base 241. In the illustrated embodiment, the base 241 is a cradle that is shaped to hold a personal communication device (e.g., smartphone). Optionally, the base 241 may include the antenna 235. In other embodiments, the base 241 may be a pad that may or may not include the antenna 235 integrated therein.

The system controller 215 is configured to receive a portable user profile from a personal communication device and/or a profile-storage system that is at a distinct location with respect to the ultrasound system 200. For example, the system controller 215 may receive the user profile from a personal communication device of the operator of the system 200. In other embodiments, the system controller may receive the user profile form the profile-storage system 120 (FIG. 1).

In some embodiments, the system controller 215 includes an identification module 233 that is configured to transmit a request to the personal communication device. The identification module 233 may be part of the loading module 230 or may be separate from the loading module 230. The request may be sent in response to determining that the personal communication device is within a range of the medical system. The request may include data for identifying the user profile associated with the operator. The request may be transmitted at different times during activation of the medical system. For example, the request may be transmitted when the operator logs onto the ultrasound system.

In embodiments in which the user has a plurality of user profiles, the loading module 230 and/or the identification module 233 may identify the user profile that should be loaded and request that type of user profile. For example, if the application that requested the user profile is for echocardiography, the loading module and/or the identification module 233 may request the user profile that corresponds to the echocardiography workflow. Alternatively, the personal communication device may determine the user profile that should be used with the medical system. If a corresponding user profile does not exist, the application may use the factory or default operational settings.

Also shown in FIG. 2, the system controller 215 may also include a data-removal module 234 that is configured to process image data to remove identifying information of a patient that is associated with the image data. For example, the operator may desire to transfer the medical image from the medical system. To this end, the operator may enter user inputs that include data-removal inputs instructing the data-removal module 234 to generate an anonymous image with the identifying information removed. The data-removal module 234 may remove the identifying information (e.g., name, identification numbers, demographic data, etc.). In some embodiments, after the identifying information is removed, the anonymous image is stored with the user profile. Before or when the anonymous image is stored with the user profile, the anonymous image may have different identifying information coupled to the image. For example, the anonymous image may be renamed or labeled in a manner that identifies an anatomical structure shown by the anonymous image (e.g., shoulder, cross-section of liver, etc.). The re-identification may be automatic or require user inputs. The re-identifying operation may be executed by the data-removal module 234.

Figure 3:
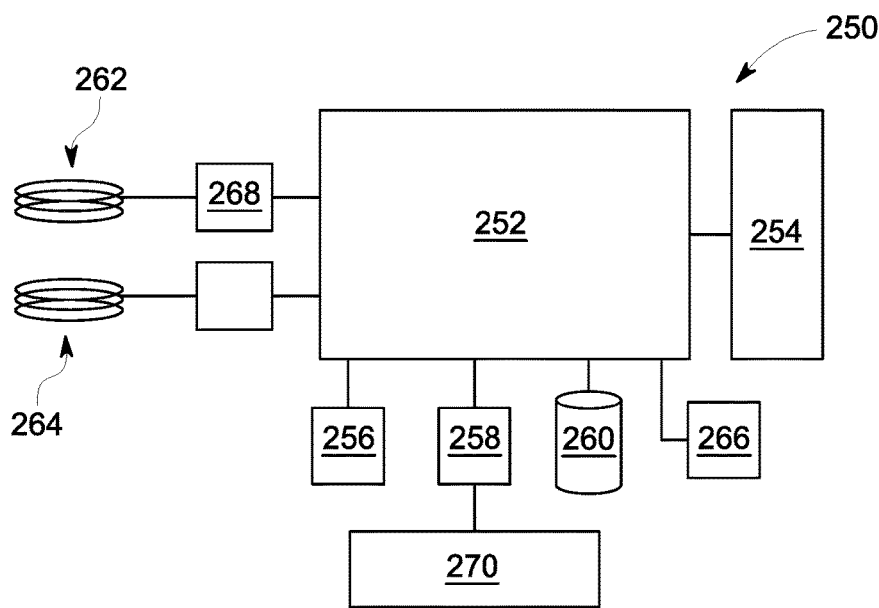
FIG. 3 illustrates a block diagram of a personal communication device in accordance with one embodiment.

FIG. 3 illustrates a block diagram of a personal communication device 250 that may be used with the system network 100 (FIG. 1), the medical systems 104A-104C (FIG. 1), and/or the ultrasound system 200. In particular embodiments, the personal communication device 250 is a smartphone or a smartwatch. It should be understood, however, that the personal communication device may be other types in other embodiments.

The device 250 includes circuitry designed to carry out the intended purpose of the device 250 (e.g., smartphone, tablet, smartwatch, etc.). The device 250 may include, among other things, a host processor 252, a power management unit (PMU) 254, one or more sensors 256, a touchscreen controller 258, memory 260, an antenna 262, one or more other antenna 264 (e.g., cellular, Bluetooth), and one or more secure elements (e.g., embedded, removable) 266. The antenna 262 is communicatively coupled to the host processor 252 using a short-range controller 268, which manages emission and reception of signals, among other things. The short-range controller 268 and the antenna 262 may be configured to communicate in accordance with a designated short-range wireless communication technology, such as NFC. The touchscreen controller 258 communicatively couples a touchscreen 270 to the host processor 252.

Figure 4:
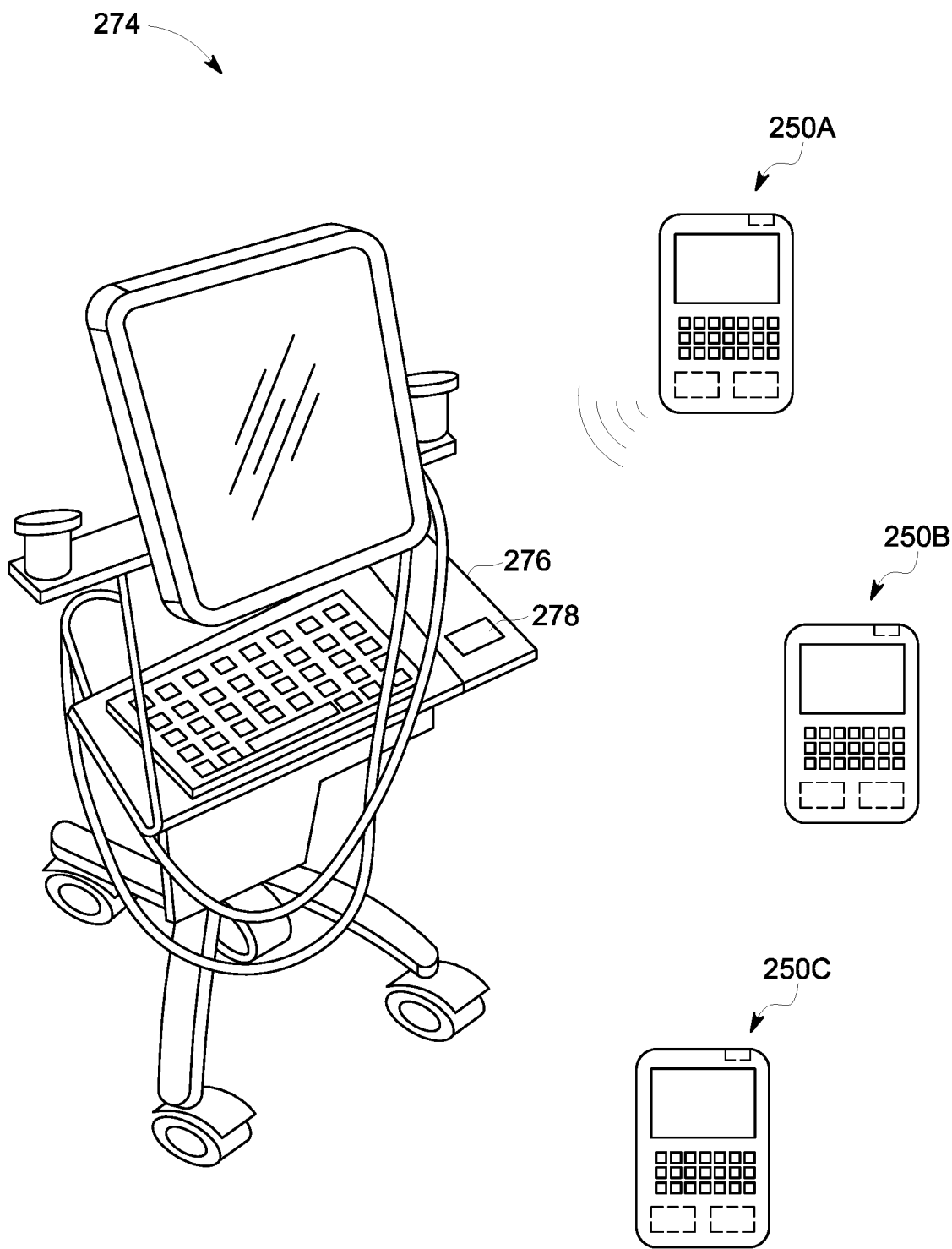
FIG. 4 illustrate a medical system having multiple personal communication devices that are operably near the medical system in accordance with an embodiment.

FIG. 4 illustrates a medical system 274 having multiple personal communication devices 250A, 250B, and 250C that are operably near the medical system 274. The medical system 274 is an ultrasound system in the illustrated embodiment, but may be other types of medical systems. The medical system 274 may have a reader device 276 (or system communication device) or may be positioned adjacent to the reader device 276. The reader device 276 may have an antenna 278. The reader device 276 may be configured to communicate with the personal communication devices 250A, 250B, 250C through one or more predetermined wireless technologies. For example, the wireless technologies may include NFC, RFID, WiFi, and/or Bluetooth. In particular embodiments, the reader device 276 is configured to communicate with the personal communication devices 250A, 250B, 250C through NFC. For example, the reader device 276 may be an NFC reader.

As used herein, the term "operably near" means that the personal communication device is sufficiently near the medical system so that the user in possession of the personal communication device may begin physically interacting with the medical system within a short period of time (e.g., less than a minute). A personal communication device may be operably near the medical system if at least one of the following exists: (a) the personal communication device is in direct communication (e.g., antenna to antenna) with the medical system through a wireless technology; (b) the personal communication device is communicatively coupled to the medical system through a short-range wireless technology; (c) the personal communication device and the medical system are within the same room or adjacent rooms; or (d) the personal communication device and the medical system are within a designated range from each other. With respect to (d), a personal communication device may be operably near the medical system when the personal communication device and the reader device of the medical system are less than 50 meters apart or less than 30 meters apart. In particular embodiments, a personal communication device may be operably near the medical system when the personal communication device and the reader device of the medical system are less than 10 meters apart or less than 1 meter apart. In more particular embodiments, a personal communication device may be operably near the medical system when the personal communication device and the reader device of the medical system are less than 10 cm apart.

In some embodiments, a personal communication device may be operably near the medical system when the personal communication device is capable of communicating directly with the medical system using a short-range wireless technology. For example, the medical system may have an NFC antenna that is configured to communicate with other NFC antennas (including NFC tags). The personal communication device may be operably near the medical system when the personal communication device is capable of communicating with the NFC antenna. The NFC antenna of the medical system may be an NFC reader or scanner that is attached to the medical system, immediately adjacent to the medical system (e.g., within a meter), or within the same room as the medical system (e.g., positioned at a doorway to the room).

The personal communication device may be configured to initiate communication with the reader device of the medical system and/or respond to a communication from the reader device. The reader device may be configured to initiate communication with the personal communication device and/or respond to a communication from the personal communication device. In some embodiments, each of the personal communication device and the reader device may be configured to initiate communication with the other.

The personal communication device may be an active device such that communication with the reader device is powered by the personal communication device. Alternatively or in addition to being active, the personal communication device may be a passive device such that communication with the reader device is powered by the reader device. For example, the personal communication device may include a tag (e.g., NFC, RFID) that is interrogated by the reader device. Similarly, the reader device may be an active device such that communication with the personal communication device is powered by the reader device. Alternatively or in addition to being active, the reader device may be a passive device such that communication with the personal communication device is powered by the personal communication device (e.g., the reader device includes a tag).

In some embodiments, the personal communication device interacts with the reader device in a reader/writer mode. For example, when the personal communication device is positioned operably adjacent to the reader device, the personal communication device may read/write data from/to the reader device. In some embodiments, the personal communication device interacts with the reader device in a card emulation mode. For example, when the personal communication device is positioned operably adjacent to the reader device, the reader device may read data stored in the personal communication device.

As shown in FIG. 4, embodiments may be configured to establish a dedicated link between a personal communication device 250A and the medical system 274 such that other users of the personal communication devices 250B, 250C are unable to use the medical system 274. This may occur, for example, when more than one healthcare provider is in the same room. In such instances, more than one personal communication device may be capable of communicating with the medical system. However, the medical system 274 may communicate exclusively with the personal communication device 250A until the user associated with the personal communication device 250A has completed the session.

Figure 5A:
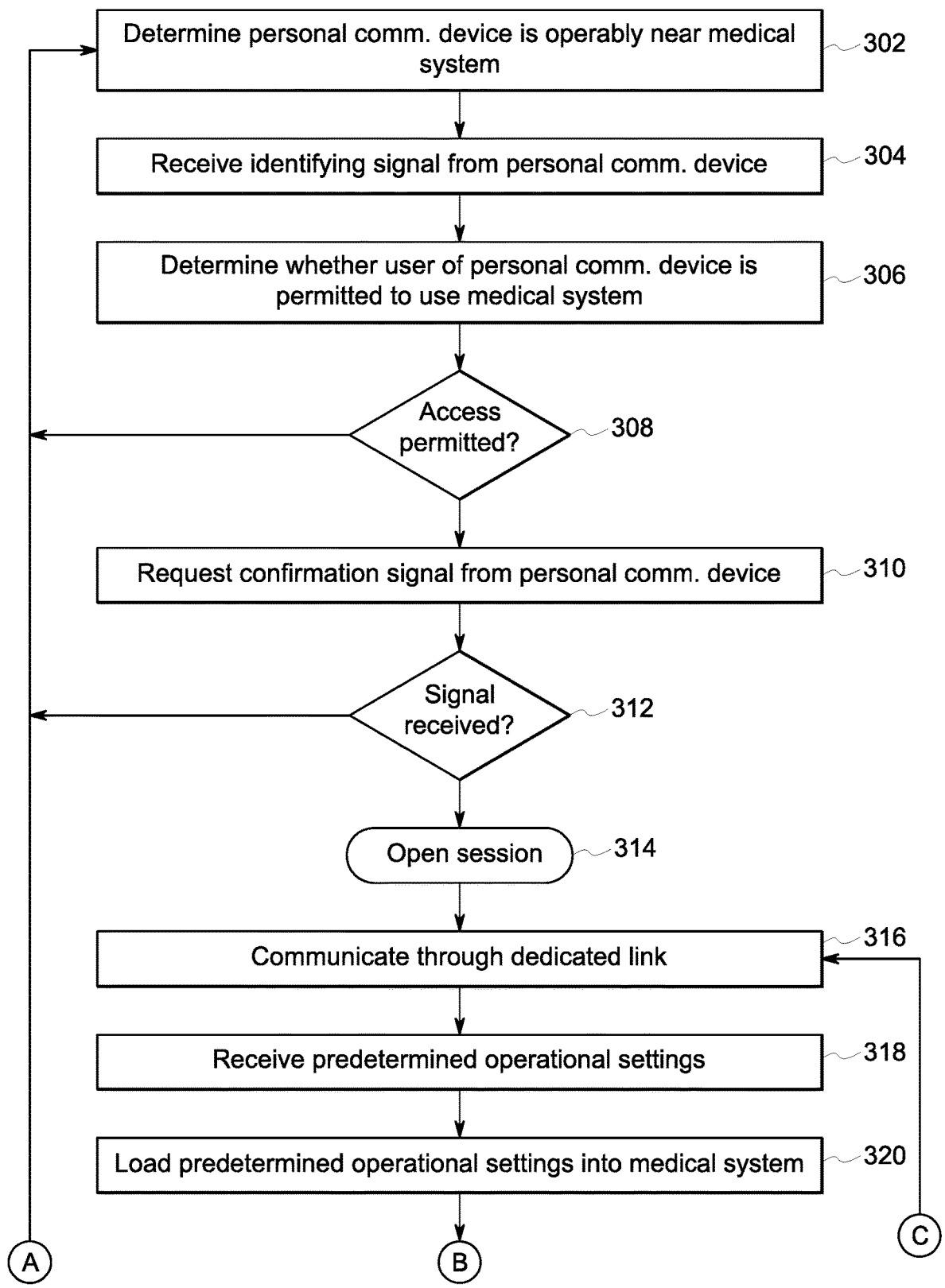
FIG. 5A is a flowchart of a portion of a method according to one embodiment.
Figure 5B:
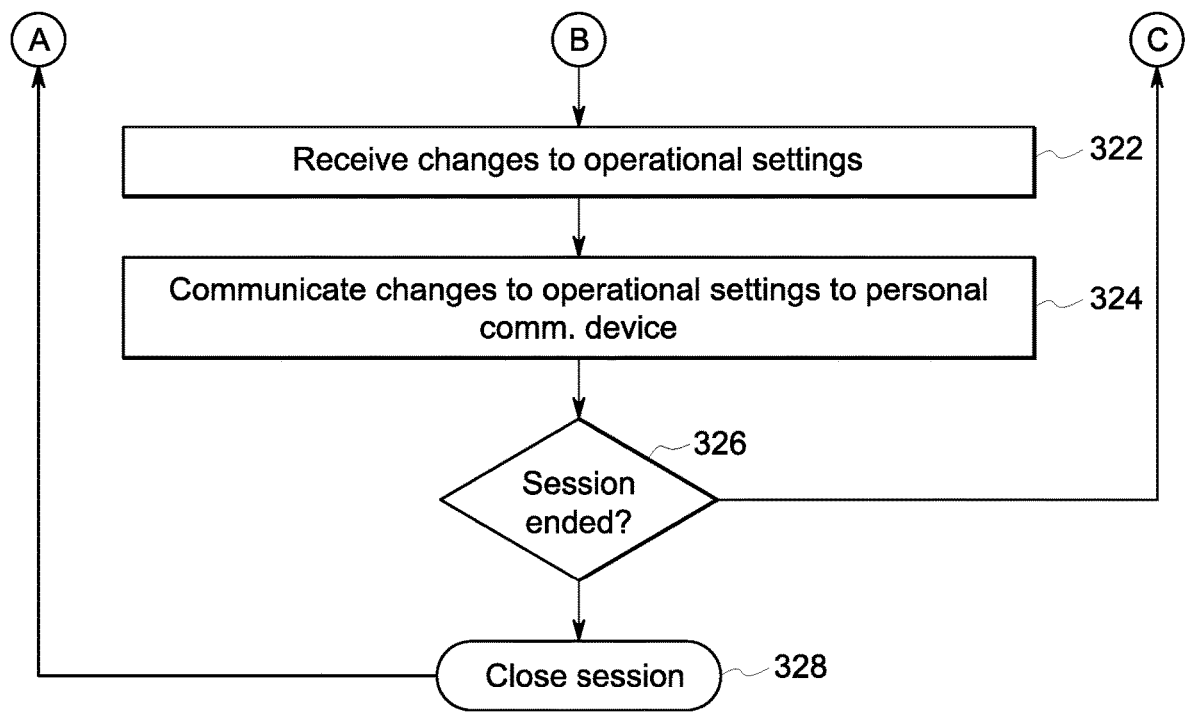
FIG. 5B is a flowchart of another portion of the method.

FIGS. 5A and 5B illustrate a flowchart of a method 300 according to one embodiment. The method 300 may be, for example, a method of granting a user access to a medical system. The method 300, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 300 may include determining, at 302, that a personal communication device is operably near a medical system (e.g., within a designated range of the medical system). As described herein, a personal communication device may be operably near a medical system if: (a) the personal communication device is in direct communication (e.g., antenna to antenna) with the medical system through a wireless technology that is different than the wireless technology used by the telecommunication network; (b) the personal communication device is communicatively coupled to the medical system through a short-range wireless technology; (c) the personal communication device and the medical system are within the same room or adjacent rooms; and/or (d) the personal communication device and the medical system are within a designated range (e.g., 30 meters) from each other.

Determining, at 302, may occur when the personal communication device and the medical system communicatively couple to each other through a short-range wireless technology. For example, the medical system may have an NFC device that repeatedly emits transmissions for initiating communication with personal communication devices. When the personal communication device is operably near the NFC device (e.g., the user in possession of the personal communication device walks into a room where the NFC device is located), the personal communication device may receive the transmission from the NFC device and emit another transmission (e.g., identifying signal). In this example, the personal communication device may be an active device or a passive device. The personal communication device may be determined, at 302, to be operably near the medical system when the personal communication device returns a communication in response to the transmissions emitted by the NFC device.

As another example, the personal communication device may have an NFC antenna that repeatedly emits transmissions for initiating communication with the medical system. When the personal communication device is within a designated range of the medical system (e.g., the user in possession of the personal communication device walks into a room where the NFC device is located), the medical system may receive the transmission from the personal communication device and emit another transmission. In this example, the personal communication device may be an active device, and the medical system may have an active device or a passive device. Thus, the personal communication device is determined to be within a designated range of the medical system when the medical system returns a communication in response to the transmissions emitted by the personal communication device.

In some embodiments, determining, at 302, may occur when a location of the personal communication device is determined to be within a designated physical distance from the medical system. For example, a tracking system of the enterprise (e.g., healthcare facility) where the medical system is located may be configured to determine a location of personal communication devices, such as devices that have been assigned or paired to the tracking system. The tracking system may be part of the system 100. Optionally, the tracking system may also be configured to determine a location of the medical systems. For example, the medical systems may be mobile and capable of moving from location to location.

The tracking system may determine the locations of the personal communication device and the medical systems using, for example, at least one of a global positioning system (GPS) or Bluetooth beacons. The personal communication device may be determined to be within a designated range of the medical system when the personal communication device and the medical system are within the same room, in adjacent rooms, or within a designated physical distance from each other. Alternatively or in addition to the above, the personal communication device may be determined to be within a designated range of the medical system when a beacon associated with the medical system detects the personal communication device.

The method 300 also includes receiving, at 304, an identifying signal from the personal communication device while the personal communication device is within the designated range of the medical system. The identifying signal may facilitate identifying the user associated with the personal communication device.

In some embodiments, the determining, at 302, and the receiving, at 304, occur at separate steps or operations. For example, when the personal communication device responds to a transmission emitted by the medical system, the transmission sent by the personal communication device may only identify the personal communication device as a device that is capable of communicating through the wireless technology. In response to determining, at 302, that the personal communication device is within a designated range of the medical system, the medical system may transmit a signal that requests the identifying signal from the personal communication device. The personal communication device may respond to this signal by sending the identifying signal.

When the medical system responds to the personal communication device after determining, at 302, that the personal communication device is within a designated range of the medical system, the medical system may communicate with the personal communication device using the same wireless technology (e.g., NFC) or using a different wireless technology. For example, after determining, at 302, that the personal communication device is within a designated range of the medical system, the medical system may then send a transmission to the personal communication device through a WiFi network or through a cellular network. Such embodiments may be suitable when, for example, the medical system includes an NFC reader that requires the personal communication device to be adjacent to the NFC reader. After establishing that the personal communication device is operably near the medical system, the user may place the personal communication device at another location that is not readable by the NFC reader, but may communicate with the medical system using another wireless technology.

In some embodiments, the determining, at 302, and receiving, at 304, may occur in a different order. For example, when the personal communication device responds to a transmission (or communication) emitted by the medical system, the transmission sent by the personal communication device may include data that may be used to identify the user associated with the personal communication device. As such, the personal communication device may be determined to be operably near, at 302, after receiving the identifying signal at 304.

At 306, it may be determined that the user associated with the personal communication device is permitted to use the medical system. If the user is permitted to use the medical system, at 308, a session with the medical system may be opened at 314. Determining, at 306, that the user associated with the personal communication device is permitted to use the medical system may occur by analyzing a database that includes a list of users that are permitted to use the medical system. Alternatively or in addition to analyzing the list, the identifying signal sent by the personal communication device may include data (e.g., a code) that indicates the user is authorized to use the medical system.

In some embodiments, the medical system includes a predetermined space where the personal communication device is positioned to provide the identifying signal. For example, the predetermined space may include or be positioned adjacent to a reader device, such as the reader device 239 or the reader device 276. In particular embodiments, the reader device is a near-field communication (NFC) device. The predetermined space may be, for example, within 10 cm of the antenna of the reader device. In some embodiments, the predetermined space is defined by a base or cradle that is shaped to hold the personal communication device.

Optionally, the method 300 may include requesting, at 310, confirmation that the possessor of the personal communication device is the user that is permitted to use the medical system. For example, the requesting, at 310, may include requesting a confirmation signal from the personal communication device. The confirmation signal may be sent from the personal communication device by, for example, entering predetermined user inputs (e.g., passcode or other information) into the personal communication device. Alternatively, the confirmation may be provided by the user of the personal communication device entering predetermined user inputs at the medical system. The user inputs entered at the personal communication device or the medical system may be, for example, a passcode, a password, voice confirmation, or confirmation using biometric data. For embodiments that include requesting, at 310, confirmation that the possessor of the personal communication device is the user that is permitted to use the medical system, a session may be opened after determining, at 312, that the confirmation has been received.

In some cases, the requesting, at 310, may include sending requests to multiple personal communication devices. In some cases, the requesting, at 310, may include sending a request to a second personal communication device after sending a request to a first personal communication device. Such instances may occur when a first healthcare provider that is associated with the first personal communication device does not wish to use the medical system, but a second healthcare provider, who entered the room after the first healthcare provider, does desire to use the medical system. After determining, at 312, that confirmation from the second personal communication device has been received, a session may be opened, at 314, for the second healthcare provider. Optionally, a dedicated link between the personal communication device and the medical system is established.

Optionally, the identifying signal that is received at 304 and/or the confirmation signal that is received at 312 may be transmitted when the personal communication device is positioned within a predetermined space. For example, the personal communication device may be positioned on a cradle that holds the personal communication device.

Optionally, the identifying signal that is received at 304 and/or the confirmation signal that is received at 312 is transmitted by the personal communication device in response to the user unlocking the personal communication device. When a personal communication device is locked, the personal communication device has limited functions. For example, a locked smartphone may only be able to make emergency calls. When locked, the personal communication device may present a predetermined screen to the user prior to granting access to the personal communication device. The predetermined screen may be configured to receive user inputs to allow access to the personal communication device.

In some embodiments, the signal (e.g., the identifying signal or the confirmation signal) is sent in response to the user entering correct user inputs for unlocking the personal communication device. In such instances, the signal sent by the personal communication device may be referred to as an "unlocked signal," because the signal was sent in response to the personal communication device being unlocked. The personal communication device may have a program running therein that sends the signal in response to the personal communication device being unlocked.

Accordingly, determining that the user associated with the personal communication device is permitted to use the medical system, at 306, may include receiving an unlocked signal from the personal communication device. The unlocked signal may be based on user inputs provided by the user while within the designated range of the medical system. Alternatively, receiving the confirmation signal, at 312, may include receiving an unlocked signal from the personal communication device. Again, the unlocked signal may be based on user inputs provided by the user while within the designated range of the medical system. In other embodiments, the signal (e.g., the identifying signal or the confirmation signal) is sent in response to opening a program (e.g., application) within the personal communication device.

Optionally, the medical system may permit the user of the personal communication device to use a device (e.g., handheld device) of the medical system. For example, an ultrasound system may unlock an ultrasound probe with respect to a base in response to receiving the signal at 312 or the session being opened at 314. After the session ends, the user may position the handheld device onto the base and the base may secure the ultrasound probe thereto. In such instances, the handheld device may be protected from being stolen or inadvertently removed.

At 316, the personal communication device and the medical system may communicate with each other. For example, the personal communication device and the medical system may communicate with each other through the dedicated link. The dedicated link is configured to prevent other users from interrupting a current session. For example, another personal communication device may become operably near the medical system during a session. The dedicated link may be established by, for example, refusing to receive or to acknowledge receiving the identifying signal from other personal communication devices. In other embodiments, the identifying signal may be acknowledged, but the medical system may send a signal indicating that the medical system is in-use.

During the session, the method 300 may also include receiving, at 318, predetermined operational settings from the personal communication device while within the designated range of the medical system. The predetermined operational settings affect operation of the medical system. The predetermined operational settings may be loaded, at 320, into the medical system so that the settings exist when the user operates the medical system. For example, the predetermined operational settings may determine image quality settings, how buttons are arranged for a user interface, color preferences for the user display (e.g., background color), and/or how data is presented to the user.

At 322, changes to the predetermined operational settings may be received. The predetermined operational settings may be changed through user inputs that occur while the user is interacting with the medical system. At 322, the changes to the predetermined operational settings may be communicated from the medical system to the personal communication device. The communicating, at 324, may occur during the session or after the session has ended. At 326, the medical system may end the session thereby permitting other users to the user the medical system.

In some embodiments, the session may end when it is determined that the personal communication device is no longer operably near the medical system. For example, the user of the personal communication device may leave the room. As another example, the user of the personal communication device may remove the device from the base. The reader device may determine that the personal communication device is no longer near and end the session. Alternatively or in addition to the above, the user may perform a designated step for ending the session. Before or after ending the session, changes to the predetermined operational settings may be stored within the personal communication device.

Each of the predetermined operational settings may be selected from a plurality of potential operational settings that control operation of the medical system. The predetermined operational settings may be loaded into the medical system as the medical system is being initiated (e.g., after the operator logs onto the medical system) or as an application is being initiated (e.g., after the operator selects an application to run). The predetermined operational settings may also be loaded into the medical system after the application using the user profile is already active.

Certain embodiments may be configured to image a patient during the session using the predetermined operational settings. In some embodiments, the predetermined operational settings affect (e.g., produce an effect upon, influence, determine, etc.) at least one of acquisition of a medical image during the imaging session or how information is displayed to the operator during the imaging session. As used herein, the operational settings "affect" the image acquisition when the operational settings at least partially determine how the image data is obtained from the patient or how the medical image is derived from the image data. For example, the operational settings may affect the ultrasound signals that are transmitted into the patient's body and/or the reception of the ultrasound signals. Operational settings affect the acquisition of the medical image when the operational settings affect how the received ultrasound signals are processed and/or analyzed to form the medical image.

The operational settings may include imaging parameters that affect the medical image (e.g., type of medical image, quality of the medical image, orientation or view of the volume of interest (VOI) in the medical image, or a size and shape of the volume of interest in the medical image). Specific examples of imaging parameters may include one or more of a depth of field of view in an ultrasound image, the gain of an ultrasound image, the frequency of ultrasound signals emitted by the probe, a focal position of the ultrasound waves emitted by the probe, and the imaging mode used to obtain the ultrasound image (e.g., B-mode, color, pulsed wave ("PW"), power Doppler Imaging ("PDI"), or M-mode imaging).

In each of the above examples, the predetermined operational setting may be an operational setting that the operator is capable of selecting among other potential operational settings. For instance, an operator may be capable of selecting the frequency to be 5 MHz over other possible frequencies. By loading the predetermined operational settings before imaging the patient, a duration of the imaging session may be shortened and/or fewer mistakes may occur. However, it should be noted that embodiments may enable the operator to change, during the imaging session, at least one of the predetermined operational settings.

In some embodiments, if the operator changes any of the predetermined operational settings, the user profile at the medical system may be updated to include the changes. After the operator has completed a workflow or decides to log out of the medical system, the medical system may synchronize the user profile at the medical system with the stored version of the user profile at the server system (or at the personal communication device). For example, the medical system may communicate with the corresponding profile-storage system to determine if the two versions of the user profile are identical. If not, the user profile at the profile-storage system may be synchronized with the user profile at the medical system. More specifically, operational settings that were changed by the operator at the medical system may be changed in the user profile at the profile-storage system. In some cases, the medical system may prompt or ask the operator if he or she desires the user profiles to be synchronized. In other embodiments, the synchronization is automatic.

Figure 6:
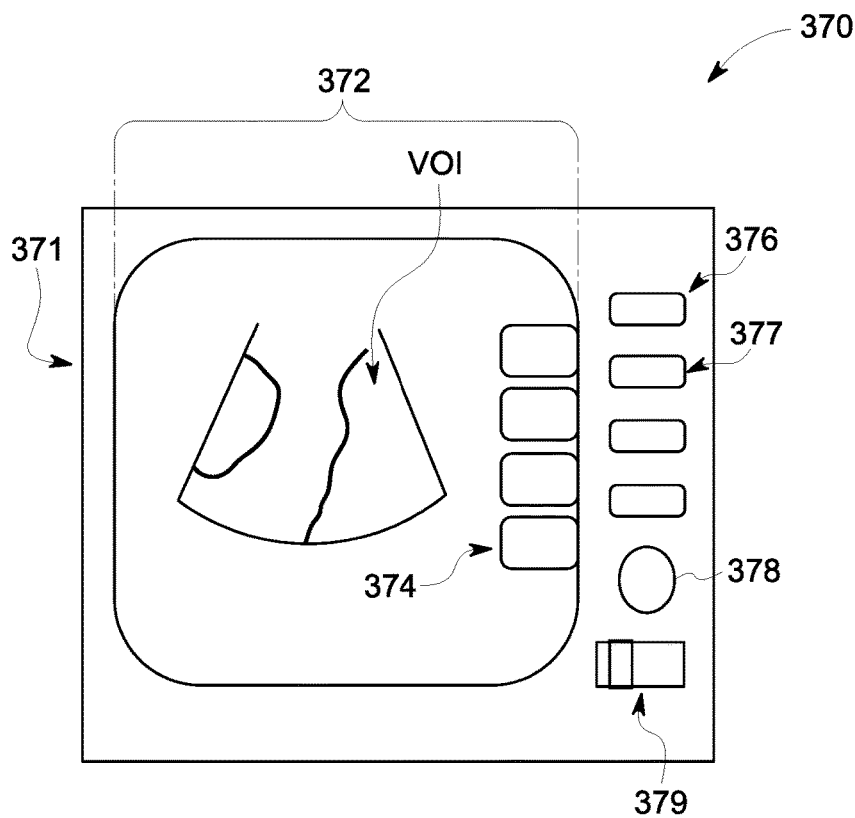
FIG. 6 illustrates a user interface that may be used with a medical system in accordance with an embodiment.

FIG. 6 illustrates a user interface 370, which may function as the user interface 222 (FIG. 2) of the ultrasound system 200. As described above, the operational settings may also affect the information that is displayed to the operator during the imaging session. For example, the operational settings may affect the type, number, and/or quality of graphics that are displayed to the operator. The operational settings may also affect a location of where graphics are located on an operator display or where user-selectable elements are located with respect to the operator. The operational settings may also designate a user-selectable element to a particular utility. As yet another example, the operational settings may also affect a timing or sequence of how information is displayed to the operator. Examples of the above are described and/or illustrated with respect to the user interface 370 in FIG. 6. However, it should be noted that the user interface 370 is exemplary only and other types, styles, and configurations of user interfaces may be implemented.

The user interface 370 may include hardware, firmware, software, or a combination thereof that enables the operator to directly or indirectly control operation of the medical system. The user interface 370 includes an operator display 371 having a display area 372 where a medical image of a VOI in a patient may be displayed. In FIG. 6, the display area 372 may be part of a touch-sensitive display (e.g., touchscreen) that can detect a presence of a touch from the operator and can also identify a location of the touch in the display area 372. As such, the touch-sensitive display may receive user inputs from the operator and also communicate information (e.g., display information) to the operator.

As shown in FIG. 6, the display area 372 may include virtual user-selectable elements 374 that are provided by, for example, a system controller such as the system controller 215. The user-selectable elements may resemble tabs or buttons on the display area 372. In addition to virtual elements, the user interface 370 may also include tangible user-selectable elements 376 that may be touched (e.g., gripped, pressed, moved, and the like) by the operator to be activated. As shown, the user-selectable elements 376 include buttons 377, a rotatable knob 378, and a slider 379.

As described above, the operational settings of the user profile may affect the type, number, and/or quality of graphics that are displayed to the operator. For example, there are four virtual user-selectable elements 374 in the display area 372. The user-selectable elements 374 may control operation of the medical system during the imaging session or provide information to the operator. The predetermined operational settings of the user profile may identify that only those user-selectable elements 374 shown in FIG. 6 may be shown during the imaging session. For example, each of the user-selectable elements 374 may represent a different stage in a workflow. If the operator does not wish to perform one portion of the workflow, then a user-selectable element that represents that portion may not be shown. Accordingly, by utilizing the portable user profile described herein, it would not be necessary for the operator to remove the user-selectable element from the display area 372.

The operational settings may also affect a location of where graphics are located on an operator display or where user-selectable elements are located with respect to the operator. In some cases, different operators may prefer different screen displays. As such, the operational settings may determine where the user-selectable elements 374 are to be located. Moreover, the operational settings may also designate a user-selectable element to a particular utility. For example, in some cases, a first operator may designate that the rotatable knob 378 be used to change gain. However, a second operator may prefer that the rotatable knob 378 be used to change the frequency or depth. Accordingly, the predetermined operational settings of the first and second operators may reflect these differences.

Moreover, the operational settings may affect a timing or sequence of when information is displayed to the operator. This may include displaying or not displaying the information entirely. For example, in some embodiments, the operator may prefer to display the imaging parameters on the display area. However, other operators may not wish to display the imaging parameters. As another example, an operator may prefer to display a representative image (e.g., an ideal image) to the operator to aid the operator in determining whether the medical image is sufficient. However, other operators may prefer to use the additional space on the display area 372 and, therefore, prefer to not include the representative image. Again, the predetermined operational settings of the first and second operators may reflect these differences.

Figure 7:
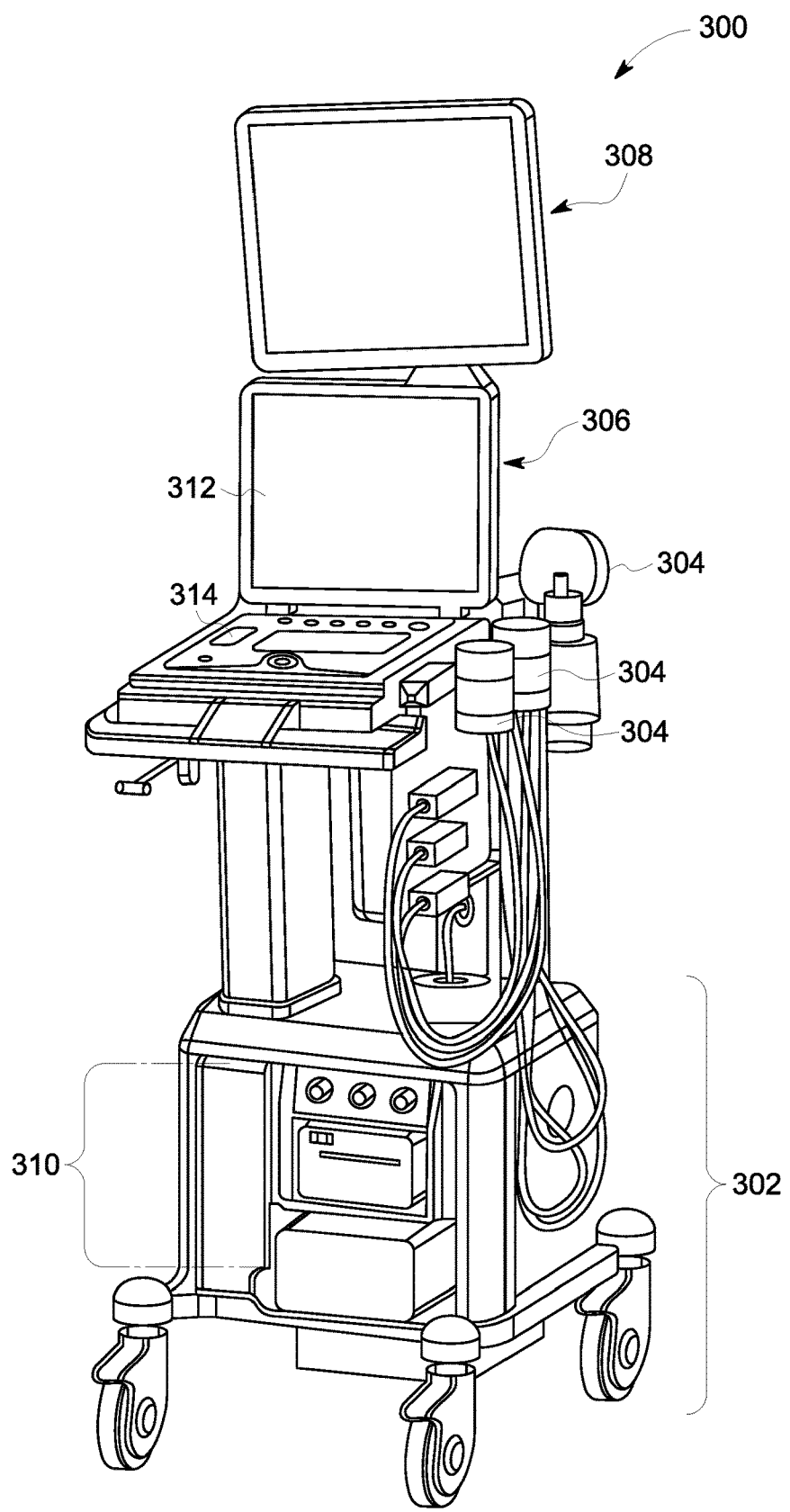
FIG. 7 is a perspective view of a console-based ultrasound system provided on a movable base in accordance with one embodiment.

FIG. 7 is a perspective view of a console-based ultrasound imaging system 300 provided on a movable base 302 in accordance with one embodiment. In particular embodiments, the medical systems (e.g., the ultrasound imaging system 300) are mobile. For embodiments that include an NFC reader, the NFC reader moves with the medical system. The system 300 may be similar to the systems 104A-104C (shown in FIG. 1) or the ultrasound system 200 (shown in FIG. 2). For example, the system 300 may include one or more transducers 304 that are similar to the transducer 206 (shown in FIG. 2), a user interface 306 that is similar to the user interface 222 (shown in FIG. 2) and a display device 308 that is similar to the display device 218 (shown in FIG. 2) in one embodiment. The system 300 includes a system controller 310 that includes one or more transmitters that may be similar to the transmitter 202 (shown in FIG. 2), a receiver (not shown) that is similar to the receiver 208 (shown in FIG. 2), a beam former (not shown) that is similar to the beam former 210 (shown in FIG. 2), an RF processor (not shown) that is similar to the RF processor 212 (shown in FIG. 2), and one or more computer-readable storage media (not shown) that are similar to one or more of the memories 214, 220 (shown in FIG. 1). The system controller 310 may be embodied in one or more computers, computing systems, microprocessors, servers, and the like. The user interface 306 may include a laptop computer having docking functionality with the movable base 302.

In the illustrated embodiment, the user interface 306 includes a secondary display device 312 and an input device 314. The secondary display device 312 may be similar to the display device 218 (shown in FIG. 2). In one embodiment, the secondary display device 312 does not include any touch sensitive portions. For example, no part of the secondary display device 312 includes a touch screen in one embodiment. As shown in FIG. 7, the input device 314 may include a keyboard. Alternatively, the input device 314 may include one or more additional or different input devices such as a mouse, microphone, and the like. The secondary display device 312 and the input device 314 are similar to the displays and input devices of known ultrasound imaging systems in one embodiment. The ultrasound data obtained by the transducer 304 and the ultrasound images formed by the controller 310 may be displayed on the secondary display device 312. One or more adjustments to the ultrasound images displayed on the secondary display device 312 may be made using the input device 314. For example, an operator may use a keystroke to change the operating frequency or imaging mode of the ultrasound image displayed on the secondary display device 312.

It should be noted that although one or more embodiments may be described in connection with an ultrasound system, the embodiments described herein are not limited to ultrasound systems. In particular, one or more embodiments may be implemented in connection with different types of medical systems.

At least one technical effect of one or more embodiments described herein includes a reduction in time for a user of a medical system to begin the process of using the medical system. Another technical effect may include loading predetermined operational settings of an operator of a medical system as the user begins a session with the medical system. By loading predetermined operational settings from a user profile, the duration of imaging sessions may be reduced.

Another technical effect may include using a personal communication device to store and transfer the user profile.

As used herein, the term "computing system" or "system controller" may include any processor-based or microprocessor-based systems including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computing system" or "system controller."

Sets of instructions may include various commands that instruct the computing system or system controller as a processing machine to perform specific operations such as the methods and processes described herein. The set of instructions may be in the form of a software program or module. The software may be in various forms such as system software or application software. Further, the software may be in the form of a collection of separate programs, a program module (or modules) within a larger program, or a portion of a program module. The software also may include modular programming in the form of object-oriented programming. The processing of input data by the processing machine may be in response to user commands, or in response to results of previous processing, or in response to a request made by another processing machine. The program is compiled to run on both 32-bit and 64-bit operating systems. A Linux-based system may also be used.

As used herein, the terms "software" and "firmware" are interchangeable, and include any computer program stored in memory for execution by a computing system, including RAM memory, ROM memory, EPROM memory, EEPROM memory, and non-volatile RAM (NVRAM) memory. The above memory types are exemplary only, and are thus not limiting as to the types of memory usable for storage of a computer program.

In yet another embodiment, a tangible non-transitory computer readable medium, excluding signals, is provided that is programmed to instruct a computing system to receive user inputs from an operator at a user interface of a medical system. The user inputs include identification data that identifies the operator. The computing system is also instructed to receive, at the medical system, a user profile from a profile-storage system that is at a distinct location with respect to the medical system. The user profile includes predetermined operational settings that are associated with the operator. The computing system is also instructed to load the predetermined operational settings into the medical system, wherein each of the predetermined operational settings is selected from a plurality of potential operational settings that control operation of the medical system. The computing system is also instructed to image a patient during an imaging session. The predetermined operational settings affect at least one of acquisition of a medical image during the imaging session or information that is displayed to the operator during the imaging session.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of various embodiments, they are by no means limiting and are only example embodiments. Many other embodiments will be apparent to those of skill in the art upon reviewing the above description. The scope of the present application should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc., are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method comprising:
    determining that a personal communication device is within a designated range of a medical system, the personal communication device configured to transmit and receive data through a telecommunication network;
    receiving an identifying signal from the personal communication device while within the designated range of the medical system for identifying a user associated with the personal communication device;
    determining that the user associated with the personal communication device is permitted to use the medical system and opening a session for the user to use the medical system;
    establishing a dedicated link between the personal communication device and the medical system such that other users are unable to use the medical system during the session;
    receiving predetermined operational settings from the personal communication device while within the designated range of the medical system, the predetermined operational settings affecting operation of the medical system, the medical system being at least one of an imaging system, diagnostic system, therapeutic system, monitoring system, or surgical system;
    communicating changes to the predetermined operational settings from the medical system to the personal communication device during the session of the user with the medical system; and
    closing the session, thereby permitting the other users to use the medical system.

2. The method of claim 1, wherein determining that the user associated with the personal communication device is permitted to use the medical system includes receiving an unlocked signal from the personal communication device, the unlocked signal being based on user inputs provided by the user while within the designated range of the medical system.

3. The method of claim 1, wherein the personal communication device is configured to present a predetermined unlock screen to the user prior to granting access to the personal communication device, the predetermined unlock screen configured to receive correct user inputs to allow access to the personal communication device, wherein determining that the user associated with the personal communication device is permitted to use the medical system includes receiving an unlocked signal from the personal communication device in response to the user entering the correct user inputs.

4. The method of claim 1, wherein determining that the personal communication device within the designated range of the medical system is determined using a first wireless technology, the method further comprising transferring data between the medical system and the personal communication device using a second wireless technology.

5. The method of claim 1, wherein the medical system is a first medical system, the method further comprising:
  determining that the personal communication device is within a designated range of a second medical system;
  receiving an identifying signal from the personal communication device while within the designated range of the second medical system;
  determining that the user associated with the personal communication device is permitted to use the second medical system and opening a session for the user to use the second medical system;
  establishing a dedicated link between the personal communication device and the second medical system such that other users are unable to access the second medical system during the session with the second medical system; and
  ending the session with the second medical system, thereby permitting the other users to use the second medical system.

6. A system comprising:
  a user interface configured to receive user inputs from a user;
  one or more processors configured to execute programmed instructions stored in memory, the one or more processors, when executing the programmed instructions, configured to:
    determine that a personal communication device is within a designated range of a medical system;
    receive an identifying signal from the personal communication device while within the designated range of the medical system for identifying the user associated with the personal communication device;
    determine that the user associated with the personal communication device is permitted to use the medical system and open a session for the user to use the medical system;
    establish a dedicated link between the personal communication device and the medical system such that other users are unable to access the medical system during the session;
    receive predetermined operational settings from the personal communication device while within the designated range of the medical system, the predetermined operational settings affecting operation of the medical system, the medical system being at least one of an imaging system, diagnostic system, therapeutic system, monitoring system, or surgical system;
    communicate changes to the predetermined operational settings from the medical system to the personal communication device during the session of the user with the medical system; and
    end the session, thereby permitting the other users to use the medical system.

7. The system of claim 6, wherein the medical system includes a predetermined space where the personal communication device is positioned to provide the identifying signal, the predetermined space including or being positioned adjacent to a near-field communication (NFC) device.

8. The system of claim 6, wherein the medical system includes a handheld device to be controlled by the user, the one or more processors configured to lock the handheld device to a base of the medical system before the session and unlock the handheld device from the base during the session.

9. The system of claim 6, wherein determining that the user associated with the personal communication device is permitted to use the medical system includes receiving an unlocked signal from the personal communication device that is different than and transmitted separately from the identifying signal.

10. The system of claim 6, wherein determining that the personal communication device is within the designated range of the medical system is determined using a first wireless technology, the one or more processors configured to transfer data between the medical system and the personal communication device using a second wireless technology.

11. The system of claim 6, wherein ending the session includes determining that the personal communication device is not operably near the medical system.

12. A method comprising:
  determining that a personal communication device is within a designated range of a first medical system, the personal communication device configured to transmit and receive data through a telecommunication network;
  receiving an identifying signal from the personal communication device while within the designated range of the first medical system for identifying a user associated with the personal communication device;
  determining that the user associated with the personal communication device is permitted to use the first medical system and opening a first session for the user to use the first medical system;
  establishing a dedicated link between the personal communication device and the first medical system such that other users are unable to use the first medical system during the first session;
  closing the first session, thereby permitting the other users to use the first medical system;
  determining that the personal communication device is within a designated range of a second medical system;
  receiving an identifying signal from the personal communication device while within the designated range of the second medical system;
  determining that the user associated with the personal communication device is permitted to use the second medical system and opening a second session for the user to use the second medical system;
  establishing a dedicated link between the personal communication device and the second medical system such that other users are unable to access the second medical system during the second session; and ending the second session, thereby permitting the other users to use the second medical system.

13. The method of claim 12, further comprising:
receiving predetermined operational settings from the personal communication device while within the designated range of the medical system, the predetermined operational settings affecting operation of the first medical system, the first medical system being at least one of an imaging system, diagnostic system, therapeutic system, monitoring system, or surgical system; and
communicating changes to the predetermined operational settings from the first medical system to the personal communication device during the session of the user with the first medical system.

14. The method of claim 12, wherein ending the session includes determining that the personal communication device is not operably near the first medical system.

15. The method of claim 12, wherein the first medical system is an ultrasound system that includes an ultrasound probe, wherein the personal communication device is at most three kilograms and is designed to have functions other than identifying a user of the personal communication device, the personal communication device including at least one of a mobile phone, a portable computer, or a wearable device.

16. A system comprising:
first and second medical systems having respective user interfaces that are configured to receive user inputs from a user;
one or more processors configured to execute programmed instructions stored in memory, the one or more processors, when executing the programmed instructions, configured to:
determine that a personal communication device is within a designated range of a first medical system;
receive an identifying signal from the personal communication device while within the designated range of the first medical system for identifying the user associated with the personal communication device;
determine that the user associated with the personal communication device is permitted to use the first medical system and open a first session for the user to use the first medical system;
establish a dedicated link between the personal communication device and the first medical system such that other users are unable to access the medical system during the first session;
end the first session, thereby permitting the other users to use the first medical system;
determining that the personal communication device is within a designated range of a second medical system;
receiving an identifying signal from the personal communication device while within the designated range of the second medical system;
determining that the user associated with the personal communication device is permitted to use the second medical system and opening a second session for the user to use the second medical system;
establishing a dedicated link between the personal communication device and the second medical system such that other users are unable to access the second medical system during the second session; and
ending the second session, thereby permitting the other users to use the second medical system.

17. The system of claim 16, wherein the first medical system includes a handheld device to be controlled by the user, the first medical system configured to lock the handheld device to a base of the medical system before the session and unlock the handheld device from the base during the session.

18. The system of claim 16, wherein the one or more processors when executing the programmed instructions also perform the following operations:
receive predetermined operational settings from the personal communication device while within the designated range of the first medical system, the predetermined operational settings affecting operation of the first medical system; and
communicate changes to the predetermined operational settings from the first medical system to the personal communication device during the session of the user with the first medical system.

19. The system of claim 16, wherein determining that the user associated with the personal communication device is permitted to use the first medical system includes receiving an unlocked signal from the personal communication device that is different than and transmitted separately from the identifying signal.

20. The system of claim 16, wherein determining that the personal communication device is within a designated range of the first medical system is determined using a first wireless technology, the one or more processors configured to transfer data between the first medical system and the personal communication device using a second wireless technology.

* * * * *